United States Patent [19]
DiGioia, III et al.

[11] Patent Number: 5,995,738
[45] Date of Patent: *Nov. 30, 1999

[54] APPARATUS AND METHOD FOR FACILITATING THE IMPLANTATION OF ARTIFICIAL COMPONENTS IN JOINTS

[75] Inventors: Anthony M. DiGioia, III, Pittsburgh, Pa.; David A. Simon, Boulder, Colo.; Branislav Jaramaz; Michael K. Blackwell, both of Pittsburgh, Pa.; Frederick M. Morgan, Quincy; Robert V. O'Toole, Brookline, both of Mass.; Takeo Kanade, Pittsburgh, Pa.

[73] Assignee: Carnegie Mellon University, Pittsburgh, Pa.

[ * ] Notice: This patent is subject to a terminal disclaimer.

[21] Appl. No.: 09/190,740

[22] Filed: Nov. 12, 1998

Related U.S. Application Data

[63] Continuation of application No. 08/803,993, Feb. 21, 1997, Pat. No. 5,880,976.

[51] Int. Cl.⁶ ............... A61F 2/32; A61F 2/34; A61F 2/36
[52] U.S. Cl. ......................... 395/500.32; 623/18
[58] Field of Search ............. 395/500.32; 364/578; 606/86, 89, 90, 91; 623/11, 16, 18, 19, 20, 21, 22, 23

[56] References Cited

U.S. PATENT DOCUMENTS

| | | | |
|---|---|---|---|
| 4,341,220 | 7/1982 | Perry | 606/130 |
| 4,905,148 | 2/1990 | Crawford | 382/131 |
| 5,007,936 | 4/1991 | Woolson | 623/23 |
| 5,086,401 | 2/1992 | Glassman et al. | 395/94 |
| 5,141,512 | 8/1992 | Farmer et al. | 606/87 |
| 5,242,455 | 9/1993 | Skeens et al. | 606/130 |
| 5,251,127 | 10/1993 | Raab | 606/130 |
| 5,299,288 | 3/1994 | Glassman et al. | 395/80 |
| 5,305,203 | 4/1994 | Raab | 606/1 |
| 5,360,446 | 11/1994 | Kennedy | 623/16 |
| 5,383,454 | 1/1995 | Bucholz | 600/429 |
| 5,389,101 | 2/1995 | Heilbrun et al. | 606/130 |
| 5,408,409 | 4/1995 | Glassman et al. | 600/407 |
| 5,517,990 | 5/1996 | Kalfas et al. | 600/414 |
| 5,682,886 | 11/1997 | Delp et al. | 600/407 |
| 5,733,338 | 3/1998 | Kampner | 623/16 |
| 5,880,976 | 3/1999 | DiGioia, III et al. | 395/500.32 |

*Primary Examiner*—Kevin J. Teska
*Assistant Examiner*—Russell W. Frejd
*Attorney, Agent, or Firm*—Kirkpatrick & Lockhart LLP

[57] ABSTRACT

Apparatuses and methods are disclosed for determining an implant position for at least one artificial component in a joint and facilitating the implantation thereof. The apparatuses and methods include creating a joint model of a patient's joint into which an artificial component is to be implanted and creating a component model of the artificial component. The joint and artificial component models are used to simulate movement in the patient's joint with the artificial component in a test position. The component model and the joint model are used to calculate a range of motion in the joint for at least one test position based on the simulated motion. An implant position, including angular orientation, in the patient's joint is determined based on a predetermined range of motion and the calculated range of motion. In a preferred embodiment, the implant position can be identified in the joint model and the joint model aligned with the joint by registering positional data from discrete points on the joint with the joint model. Such registration also allows for tracking of the joint during surgical procedures. A current preferred application of the invention is for determining the implant position and sizing of an acetabular cup and femoral implant for use in total hip replacement surgery.

24 Claims, 11 Drawing Sheets

APPARATUS AND METHOD FOR FACILITATING THE IMPLANTATION OF ARTIFICIAL COMPONENTS IN JOINTS

CROSS-REFERENCE TO RELATED APPLICATIONS

This application is a continuation of U.S. patent application Ser. No. 08/803,993, filed Feb. 21, 1997, now U.S. Pat. No. 5,880,976.

CROSS-REFERENCE TO RELATED APPLICATIONS

Not Applicable

STATEMENT REGARDING FEDERALLY SPONSORED RESEARCH OR DEVELOPMENT

This work was supported in part by a National Challenge grant from the National Science Foundation Award IRI 9422734.

BACKGROUND OF THE INVENTION

The present invention is directed generally to the implantation of artificial joint components and, more particularly, to computer assisted surgical implantation of artificial acetabular and femoral components during total hip replacement and revision procedures.

Total hip replacement (THR) or arthroplasty (THA) operations have been performed since the early 1960s to repair the acetabulum and the region surrounding it and to replace the hip components, such as the femoral head, that have degenerated. Currently, approximately 200,000 THR operations are performed annually in the United States alone, of which approximately 40,000 are redo procedures, otherwise known as revisions. The revisions become necessary due to a number of problems that may arise during the lifetime of the implanted components, such as dislocation, component wear and degradation, and loosening of the implant from the bone.

Dislocation of the femoral head from the acetabular component, or cup, is considered one of the most frequent early problems associated with THR, because of the sudden physical, and emotional, hardship brought on by the dislocation. The incidence of dislocation following the primary THR surgery is approximately 2–6% and the percentage is even higher for revisions. While dislocations can result from a variety of causes, such as soft tissue laxity and loosening of the implant, the most common cause is impingement of the femoral neck with either the rim of an acetabular cup implant, or the soft tissue or bone surrounding the implant. Impingement most frequently occurs as a result of the malposition of the acetabular cup component within the pelvis.

Some clinicians and researchers have found incidence of impingement and dislocations can be lessened if the cup is oriented specifically to provide for approximately 15° of anteversion and 45° of abduction; however, this incidence is also related to the surgical approach. For example, McCollum et al. cited a comparison of THAs reported in the orthopaedic literature that revealed a much higher incidence of dislocation in patients who had THAs with a posterolateral approach. McCollum, D. E. and W. J. Gray, "Dislocation after total hip arthroplasty (causes and prevention)", Clinical Orthopaedics and Related Research, Vol. 261, p.159–170 (1990). McCollum's data showed that when the patient is placed in the lateral position for a posterolateral THA approach, the lumbar lordotic curve is flattened and the pelvis may be flexed as much as 35°. If the cup was oriented at 15–20° of flexion with respect to the longitudinal axis of the body, when the patient stood up and the postoperative lumbar lordosis was regained, the cup could be retroverted as much as 10°–15° resulting in an unstable cup placement. Lewinnek et al. performed a study taking into account the surgical approach utilized and found that the cases falling in the zone of 15°±10° of anteversion and 40°±10° of abduction have an instability rate of 1.5%, compared with a 6% instability rate for the cases falling outside this zone. Lewinnek G. E., et al., "Dislocation after total hip-replacement arthroplasties", Journal of Bone and Joint Surgery, Vol. 60-A, No.2, p. 217–220 (March 1978). The Lewinnek work essentially verifies that dislocations can be correlated with the extent of malpositioning, as would be expected. The study does not address other variables, such as implant design and the anatomy of the individual, both of which are known to greatly affect the performance of the implant.

The design of the implant significantly affects stability as well. A number of researchers have found that the head-to-neck ratio of the femoral component is the key factor of the implant impingement, see Amstutz H. C., et al., "Range of Motion Studies for Total Hip Replacements", Clinical Orthopaedics and Related Research Vol. 111, p. 124–130 (September 1975). Krushell et al. additionally found that certain long and extra long neck designs of modular implants can have an adverse effect on the range of motion. Krushell, R. J., Burke D. W., and Harris W. H., "Range of motion in contemporary total hip arthroplasty (the impact of modular head-neck components)", The Journal of Arthroplasty, Vol. 6, p. 97–101 (February 1991). Krushell et al. also found that an optimally oriented elevated-rim liner in an acetabular cup implant may improve the joint stability with respect to implant impingement. Krushell, R. J., Burke D. W., and Harris W. H., "Elevated-rim acetabular components: Effect on range of motion and stability in total hip arthroplasty", The Journal of Arthroplasty, Vol. 6 Supplement, p. 1–6, (October 1991). Cobb et al. have shown a statistically significant reduction of dislocations in the case of elevated-rim liners, compared to standard liners. Cobb T. K., Morrey B. F., Ilstrup D. M., "The elevated-rim acetabular liner in total hip arthroplasty: Relationship to postoperative dislocation", Journal of Bone and Joint Surgery, Vol 78-A, No. 1, p. 80–86, (January 1996). The two-year probability of dislocation was 2.19% for the elevated liner, compared with 3.85% for standard liner. Initial studies by Maxian et al. using a finite element model indicate that the contact stresses and therefore the polyethylene wear are not significantly increased for elevated rim liners; however, points of impingement and subsequent angles of dislocation for different liner designs are different as would be expected. Maxian T. A., et al. "Femoral head containment in total hip arthroplasty: Standard vs. extended lip liners", 42nd Annual meeting, Orthopaedic Research society, p. 420, Atlanta, Ga. (Feb. 19–22, 1996); and Maxian T. A., et al. "Finite element modeling of dislocation propensity in total hip arthroplasty", 42nd Annual meeting, Orthopaedic Research society, p. 259–64, Atlanta, Ga. (Feb. 19–22, 1996).

An equally important concern in evaluating the dislocation propensity of an implant are variations in individual anatomies. As a result of anatomical variations, there is no single optimal design and orientation of hip replacement components and surgical procedure to minimize the dislocation propensity of the implant. For example, the pelvis can assume different positions and orientations depending or whether an individual is lying supine (as during a CT-scan or routine X-rays), in the lateral decubitis position (as during surgery) or in critical positions during activities of normal daily living (like bending over to tie shoes or during normal gait). The relative position of the pelvis and leg when defining a "neutral" plane from which the angles of movement, anteversion, abduction, etc., are calculated will significantly influence the measured amount of motion permitted before impingement and dislocation occurs. Therefore, it is necessary to uniquely define both the neutral orientation of the femur relative to the pelvis for relevant positions and activities, and the relations between the femur with respect to the pelvis of the patient during each segment of leg motion.

Currently, most planning for acetabular implant placement and size selection is performed using acetate templates and a single anterior-posterior x-ray of the pelvis. Acetabular templating is most useful for determining the approximate size of the acetabular component; however, it is only of limited utility for positioning of the implant because the x-rays provide only a two dimensional image of the pelvis. Also, the variations in pelvic orientation can not be more fully considered as discussed above.

Intra-operative positioning devices currently used by surgeons attempt to align the acetabular component with respect to the sagittal and coronal planes of the patient. B. F. Morrey, editor, "Reconstructive Surgery of the Joints", chapter Joint Replacement Arthroplasty, pages 605–608, Churchill Livingston, 1996. These devices assume that the patient's pelvis and trunk are aligned in a known orientation, and do not take into account individual variations in a patient's anatomy or pelvic position on the operating room table. These types of positioners can lead to a wide discrepancy between the desired and actual implant placement, possibly resulting in reduced range of motion, impingement and subsequent dislocation.

Several attempts have been made to more precisely prepare the acetabular region for the implant components. U.S. Pat. No. 5,007,936 issued to Woolson is directed to establishing a reference plane through which the acetabulum can be reamed and generally prepared to receive the acetabular cup implant. The method provides for establishing the reference plane based on selecting three reference points, preferably the 12 o'clock position on the superior rim of the acetabulum and two other reference points, such as a point in the posterior rim and the inner wall, that are a known distance from the superior rim. The location of the superior rim is determined by performing a series of computed tomography (CT) scans that are concentrated near the superior rim and other reference locations in the acetabular region.

In the Woolson method, calculations are then performed to determine a plane in which the rim of the acetabular cup should be positioned to allow for a predetermined rotation of the femoral head in the cup. The distances between the points and the plane are calculated and an orientation jig is calibrated to define the plane when the jig is mounted on the reference points. During the surgical procedure, the surgeon must identify the 12 o'clock orientation of the superior rim and the reference points. In the preferred mode, the jig is fixed to the acetabulum by drilling a hole through the reference point on the inner wall of the acetabulum and affixing the jig to the acetabulum. The jig incorporates a drill guide to provide for reaming of the acetabulum in the selected plane.

A number of difficulties exist with the Woolson method. For example, the preferred method requires drilling a hole in the acetabulum. Also, visual recognition of the reference points must be required and precision placement on the jig on reference points is performed in a surgical setting. In addition, proper alignment of the reaming device does not ensure that the implant will be properly positioned, thereby establishing a more lengthy and costly procedure with no guarantees of better results. These problems may be a reason why the Woolson method has not gained widespread acceptance in the medical community.

In U.S. Pat. Nos. 5,251,127 and 5,305,203 issued to Raab, a computer-aided surgery apparatus is disclosed in which a reference jig is attached to a double self indexing screw, previously attached to the patient, to provide for a more consistent alignment of the cutting instruments similar to that of Woolson. However, unlike Woolson, Raab et al. employ a digitizer and a computer to determine and relate the orientation of the reference jig and the patient during surgery with the skeletal shapes determined by tomography.

Similarly, U.S. Pat. Nos. 5,086,401, 5,299,288 and 5,408,409 issued to Glassman et al. disclose an image directed surgical robotic system for reaming a human femur to accept a femoral stem and head implant using a robot cutter system. In the system, at least three locating pins are inserted in the femur and CT scans of the femur in the region containing the locating pins are performed. During the implanting procedure, the locating pins are identified on the patient, as discussed in col. 9, lines 19–68 of Glassman's '401 patent. The location of the pins during the surgery are used by a computer to transform CT scan coordinates into the robot cutter coordinates, which are used to guide the robot cutter during reaming operations.

While the Woolson, Raab and Glassman patents provide methods and apparatuses that further offer the potential for increased accuracy and consistency in the preparation of the acetabular region to receive implant components, there remain a number of difficulties with the procedures. A significant shortcoming of the methods and apparatuses is that when used for implanting components in a joint there are underlying assumptions that the proper position for the placement of the components in the joints has been determined and provided as input to the methods and apparatuses that are used to prepare the site. As such, the utility and benefit of the methods and apparatuses are based upon the correctness and quality of the implant position provided as input to the methods.

In addition, both the Raab and Glassman methods and apparatuses require that fiducial markers be attached to the patient prior to performing tomography of the patients. Following the tomography, the markers must either remain attached to the patient until the surgical procedure is performed or the markers must be reattached at the precise locations to allow the transformation of the tomographic data to the robotic coordinate system, either of which is undesirable and/or difficult in practice.

Thus, the need exists for apparatuses and methods which overcome, among others, the above-discussed problems so as to provide for the proper placement and implantation of the joint components to provide an improved range of motion and usage of the joint following joint reconstruction, replacement and revision surgery.

BRIEF SUMMARY OF THE INVENTION

The above objectives and others are accomplished by methods and apparatuses in accordance with the present invention. The apparatuses and methods include creating a joint model of a patient's joint into which an artificial component is to be implanted and creating a component model of the artificial component. The joint and artificial component models are used to simulate movement of the patient's joint with the artificial component in a test position. The component model and the joint model are used to calculate a range of motion of the joint for at least one test position based on the simulated movement. An implant position, including angular orientation, for the artificial component is determined based on a predetermined range of motion and the calculated range of motion. A goal of the simulation process is to find the implant position which optimizes the calculated range of motion using the predetermined range of motion as a basis for optimization. In practice, the predetermined range of motion is determined based on desired functional motions selected by a medical practitioner on a patient specific basis (e.g. sitting requires flexion of 90°). In a preferred embodiment, the implant position can be identified in the joint model. During surgery the joint model can be aligned with the joint by registering positional data from discrete points on the joint with the joint model. Such registration also allows for tracking of the joint during the surgical procedures.

A current preferred application of the invention is for determining the implant position and sizing of an acetabular cup and femoral implant for use in total hip replacement surgery. Also in a preferred embodiment, alignment of the joint model with the patient's joint is performed using surface based registration techniques. The tracking of the pelvis, the acetabular cup, femoral implant, and surgical instrument is preferably performed using an emitter/detector optical tracking system.

The present invention provides the medical practitioner a tool to precisely determine an optimal size and position of artificial components in a joint to provide a desired range of motion of the joint following surgery and to substantially lessen the possibility of subsequent dislocation. Accordingly, the present invention provides an effective solution to problems heretofore encountered with precisely determining the proper sizing and placement of an artificial component to be implanted in a joint. In addition, the practitioner is afforded a less invasive method for executing the surgical procedure in accordance with the present invention. These advantages and others will become apparent from the following detailed description.

BRIEF DESCRIPTION OF THE DRAWINGS

A preferred embodiment of the invention will now be described, by way of example only, with reference to the accompanying figures wherein like members bear like reference numerals and wherein.

DETAILED DESCRIPTION OF THE INVENTION

Figure 1:
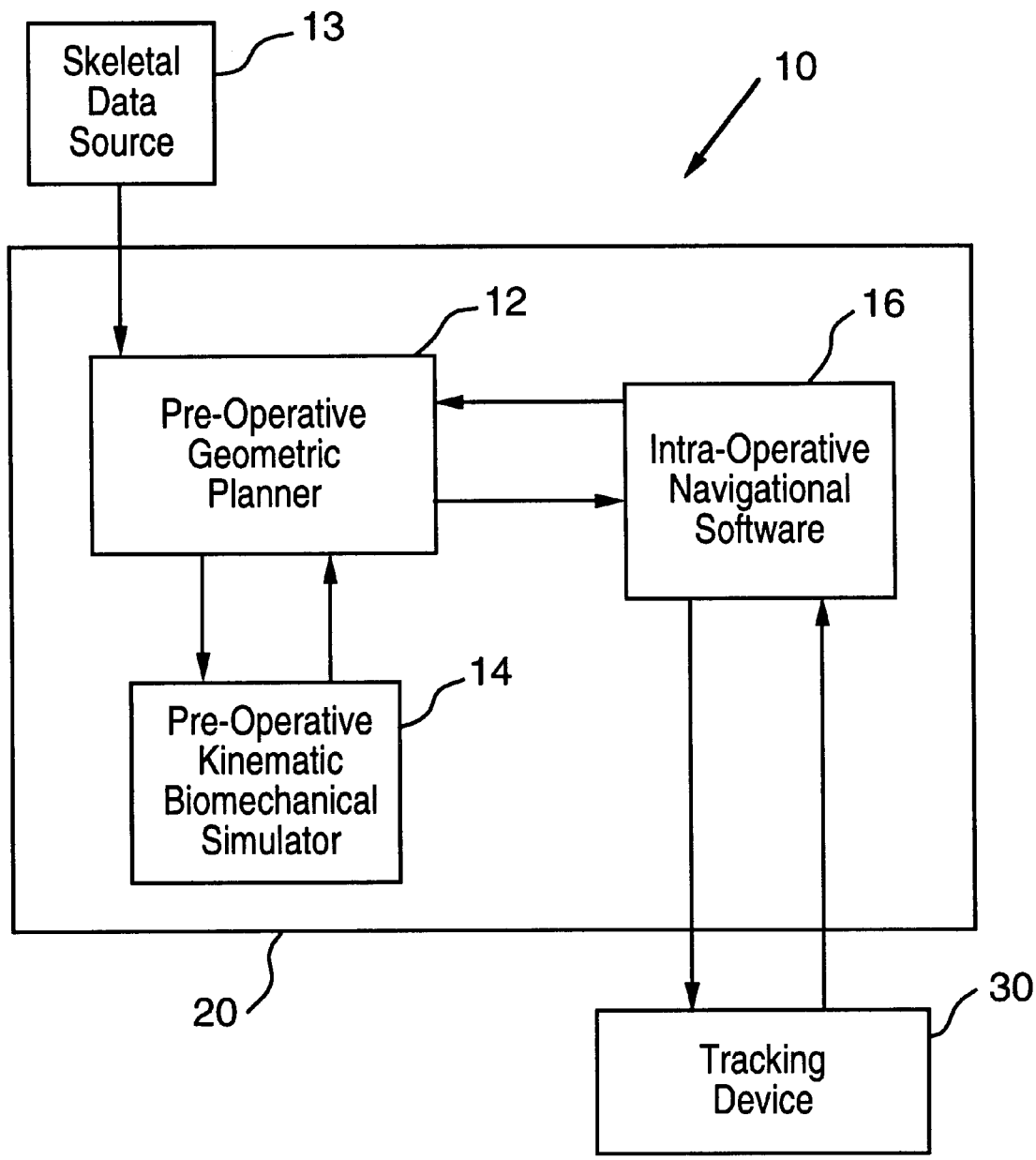
FIG. 1 is a system overview of a preferred embodiment of the present invention.

The apparatus 10 of the present invention will be described generally with reference to the drawings for the purpose of illustrating the present preferred embodiments of the invention only and not for purposes of limiting the same. A system overview is provided in FIG. 1 and general description of the method of the present invention is presented in flow chart form in FIG. 2. The apparatus 10 includes a geometric pre-operative planner 12 that is used to create geometric models of the joint and the components to be implanted based on geometric data received from a skeletal structure data source 13. The pre-operative planner 12 is interfaced with a pre-operative kinematic biomechanical simulator 14 that simulates movement of the joint using the geometric models for use in determining implant positions, including angular orientations, for the components. The implant positions are used in conjunction with the geometric models in intra-operative navigational software 16 to guide a medical practitioner in the placement of the implant components at the implant positions.

Figure 3:
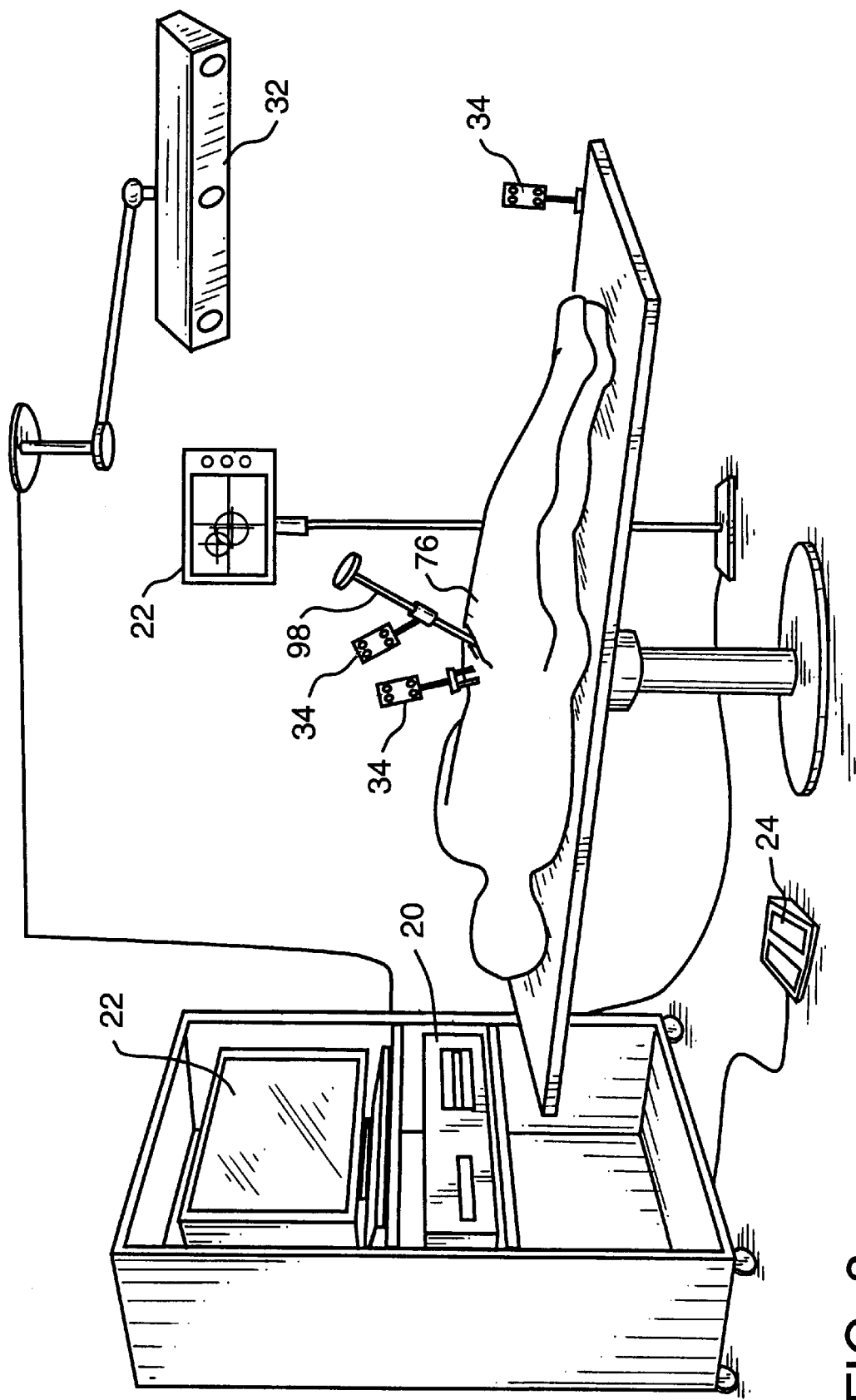
FIG. 3 is a schematic layout of the apparatus of the present invention being used in a hip replacement procedure.

The pre-operative geometric planner 12, the pre-operative kinematic biomechanical simulator 14 and the intra-operative navigational software are implemented using a computer system 20 having at least one display monitor 22, as shown in FIG. 3. For example, applicants have found that a Silicon Graphics O2 workstation (Mountain View, Calif.) can be suitably employed as the computer system 20; however, the choice of computer system 20 will necessarily depend upon the resolution and calculational detail sought in practice. During the pre-operative stages of the method, the display monitor 22 is used for viewing and interactively creating and/or generating models in the pre-operative planner 12 and displaying the results of the biomechanical simulator 14. The pre-operative stages of the method may be carried out on a computer (not shown) remote from the surgical theater.

During the intra-operative stages of the method, the computer system 20 is used to display the relative locations of the objects being tracked with a tracking device 30. The medical practitioner preferably can control the operation of the computer system 20 during the procedure, such as through the use of a foot pedal controller 24 connected to the computer system 20. The tracking device 30 can employ any type of tracking method as may be known in the art, for example, emitter/detector systems including optic, acoustic or other wave forms, shape based recognition tracking algorithms, or video-based, mechanical, electromagnetic and radio frequency (RF) systems. In a preferred embodiment, schematically shown in FIG. 3, the tracking device 30 is an optical tracking system that includes at least one camera 32 that is attached to the computer system 20 and positioned to detect light emitted from a number of special light emitting diodes, or targets 34. The targets 34 can be attached to bones, tools, and other objects in the operating room equipment to provide precision tracking of the objects. One such device that has been found to be suitable for performing the tracking function is the Optotrak™ 3020 system from Northern Digital Inc., Ontario, Canada, which is advertised as capable of achieving accuracies of roughly 0.1 mm at speeds of 100 measurements per second or higher.

Figure 2:
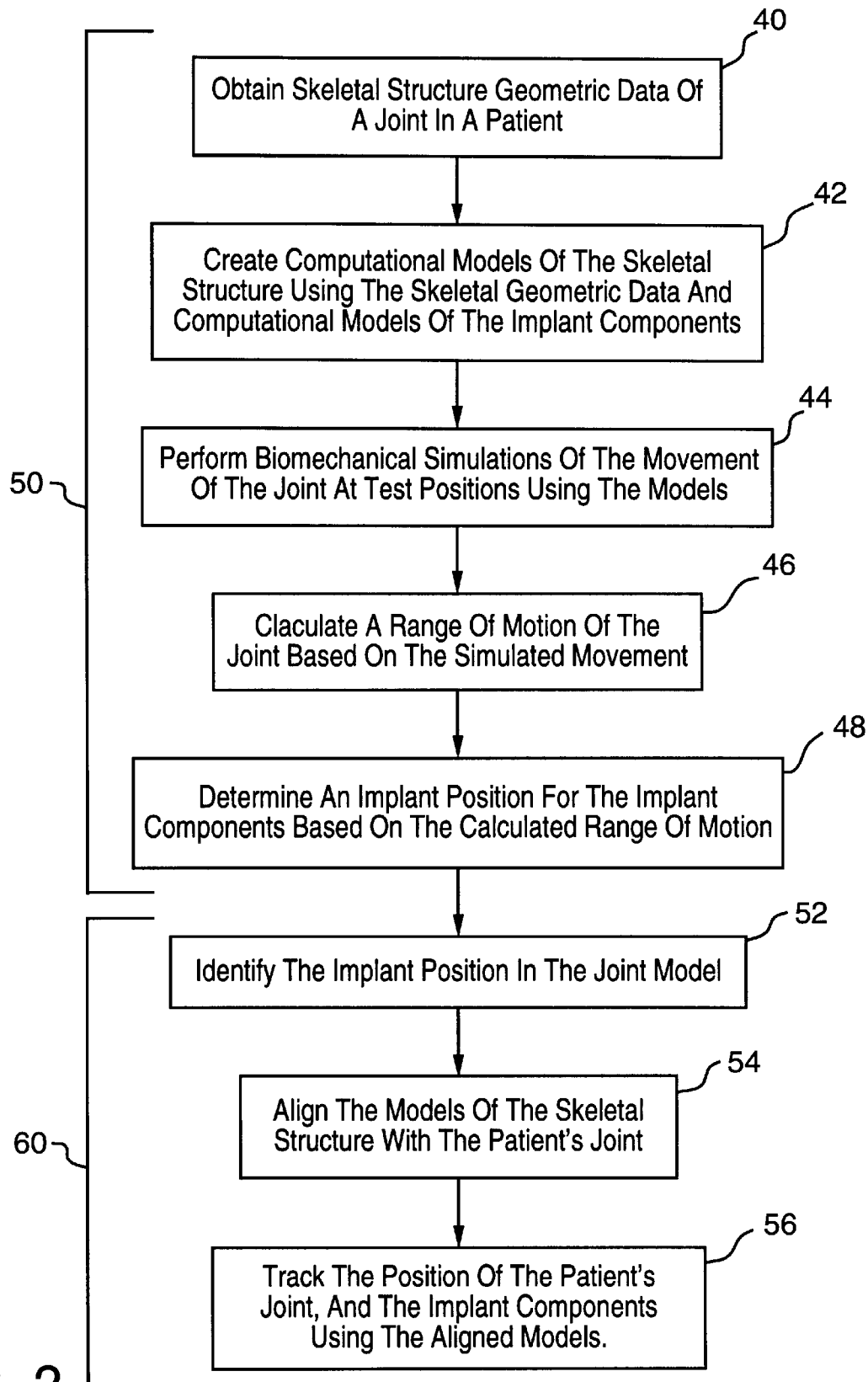
FIG. 2 is a flow chart illustrating the method of the present invention.

The apparatus 10 of FIG. 1 is operated in accordance with the method illustrated in FIG. 2. The skeletal structure of the joint is determined at step 40 using tomographic data (three dimensional) or computed tomographic data (pseudo three dimensional data produced from a series of two dimensional scans) or other techniques from the skeletal data source 13. Commonly used tomographic techniques include computed tomography (CT), magnetic resonance imaging (MRI), positron emission tomographic (PET), or ultrasound scanning of the joint and surround structure. The tomographic data from the scanned structure generated by the skeletal data source 13 is provided to the geometric planner 12 for use in producing a model of the skeletal structure. It should be noted that, in a preferred embodiment, there is no requirement that fiducial markers be attached to the patient in the scanned region to provide a reference frame for relating the tomography scans to intra-operative position of the patient, although markers can be used as a cross reference or for use with other alternative embodiments.

At step 42, a surface model is created, or constructed, from the skeletal geometric data using techniques, such as those described by B. Geiger in "Three-dimensional modeling of human organs and its application to diagnosis and surgical planning", Ph.D. thesis, Ecole des Mines de Paris, April 1993. The geometric models constructed from the skeletal data source 13 can be manually generated and input to the geometric planner 12, but it is preferable that the data be used to create the geometric models in an automated fashion.

Also at step 42, geometric models of the artificial components to be implanted into the joint are created/generated. The geometric models can be created in any manner as is known in the art including those techniques described for creating joint models. The geometric models of the artificial components can be used in conjunction with the joint model to determine an initial static estimate of the proper size of the artificial components to be implanted.

In step 44, the geometric models of the joint and the artificial components are used to perform biomechanical simulations of the movement of the joint containing the implanted artificial components. The biomechanical simulations are preferably performed at a number of test positions to dynamically optimize the size, position and orientation of the artificial components in the patient's joint to achieve a predetermined range of motion following surgery. The predetermined range of motion for a particular patient is determined based on the expected activities of the patient following surgery. For example, with regard to hip functions, daily activities, such as getting out of bed, walking, sitting and climbing stairs, that are performed by individuals requiring different ranges of motion, as will be discussed in further detail below.

The size and orientations of the implant component, and movements simulated at various test positions used in step 44 can be fully automated or manually controlled. In a preferred embodiment, the selection and test process would be automated so as to be more fully optimizable to a predetermined range of motion, either generally, or for predetermined activity. However, because it is necessary that medical practitioners be comfortable and develop confidence in the system, manual control is provided over the selection of the implant components and the test positions in the biomechanical simulator 14.

In step 46, the simulated movement of the joint at various implant positions is used to calculate a range of motion for each implant position. In step 48, the calculated ranges of motion are compared to the predetermined range of motion to select an implant position for the artificial components. A goal of the simulation process is to find the implant position which optimizes the calculated range of motion using the predetermined range of motion as a basis for optimization. In practice, the predetermined range of motion is determined based on desired functional motions selected by a medical practitioner on a patient specific basis (e.g. sitting requires flexion of 90°). The determination of the implant position can be further influenced by others factors such as the variation in the calculated range of motion as a function of implant component orientation. This criterion is useful for determining the surgical margin of error that is available to the medical practitioner without a substantial diminution in the range of motion of the joint.

Steps 40, 42, 44, 46 and 48 represent a pre-operative procedure 50 which is performed so that the artificial components can be properly sized and implant positions can be properly determined. The remainder of the steps in FIG. 2, steps 52, 54, and 56 comprise a procedure 60 which enables a surgeon to realize the desired implant position in the surgical theater.

In step 52, the implant positions determined using procedure 50 are then identified, by marking or incorporating the information in some appropriate manner in the geometric model of the joint. The geometric models of the joint and the artificial components can then be used in conjunction with positional data obtained from the joint and the artificial components during a surgical procedure to provide intra-operative guidance for the implantation of the artificial components.

In step 54, the joint model based on the skeletal data is aligned with the intra-operative position of the patient's joint. In a preferred embodiment, step 54 is performed using a technique known as three dimensional (3D) surface registration. In 3D surface registration, discrete registration points are obtained from the joint skeletal structure to define the intra-operative position of the patient's joint. The registration points are fitted to the joint model of the skeletal structure to determine a coordinate transformation that is used to align the joint model with the intra-operative position of the patient's joint. Once the transformation is established, the intra-operative position of the patient's joint can be tracked using the joint model by obtaining positional data from a point on the joint that provides spatial correspondence between the pre-operative models and the intra-operative measurements. A more thorough description of the surface registration procedure is discussed in D. A. Simon, M. Hebert, and T. Kanade, "Real-time 3-D Pose Estimation Using a High-Speed Range Sensor", Carnegie Mellon University, Robotics Institute Technical Report CMU-RI-TR-93-24 (November 1993); D. A. Simon, M. Hebert, and T. Kanade, "Techniques for fast and accurate intra-surgical registration", Journal of Image Guided Surgery, 1(1): 17–29, (April 1995); and D. A. Simon, et al., "Accuracy validation in image-guided orthopaedic surgery", Proc. 2nd Int'l Symp. MRCAS, Baltimore, (Nov. 1995), which are incorporated herein by reference.

The physical location of the intra-operative registration points on the joint from which the positional data is obtained will determine the amount of positional data required to uniquely determine and align the geometric model with the registration points. For example, it is desirable to obtain positional data from the joint that will maximize the constraint on the possible solutions to the alignment problem and provide high level of sensitivity to variations in the position, including orientation, of the joint, as discussed above in the Simon et al. references. The goal of the registration process is to determine a "registration transformation" which best aligns the discrete points that provide the spatial position and orientation of the joint with the joint models. Preferably, an initial estimate of this transformation is first determined using manually specified anatomical landmarks to perform corresponding point registration. Once this initial estimate is determined, the surface-based registration algorithm uses the pre- and intra-operative data to refine the initial transformation estimate.

Alternatively, step 54 can be implemented using registration systems that employ fiducial markers, to align the pre-operative data with the intra-operative position of the patient's joint. In those methods, the fiducial markers must be surgically implanted into the skeletal structure before pre-operative images are acquired in step 40. The intra-operative position of the fiducial markers are compared to the pre-operative data to determine the position of the patient's joint. An example of such a fiducial marker system is discussed in R. H. Taylor, et al., "An image-directed robotic system for precise orthopaedic surgery", IEEE Trans. on Robotics and Automation, 10(3): 261–275, June 1994. In addition, step 54 can be implemented using other registration systems that do not require the pre-operative use of fiducial markers.

In step 56, the position of the joint and the implant components are tracked and compared in near real time to the implant position identified in the joint model. In this step, the tracking device 30 provides the positional data representative of the position of the patient's joint to the computer system 20. The computer system 20 employs registration routines within the intra-operative navigational software 16 to determine the position and orientation of the joint and then displays the relative positions of the artificial component and the implant position. The tracking device 30 can also be used to track and provide positional data representative of the position of other physical objects in the operating room, such as surgical instruments. Additional details of the methods and apparatuses are presented in "HipNav: Pre-operative Planning and Intra-operative Navigational Guidance for Acetabular Implant Placement in Total Hip Replacement Surgery". DiGioia et al., $2^{nd}$ CAOS Symposium, Bern, Switzerland, 1996, which is incorporated herein by reference.

Figure 4C:
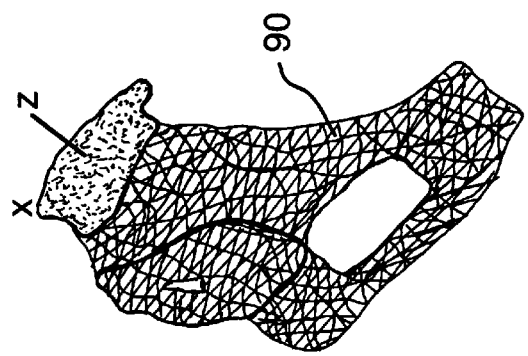
FIGS. 4(a–c) show the creation of the pelvic model using two dimensional scans of the pelvis (a), from which skeletal geometric data is extracted as shown in (b) and used to create the pelvic model (c)
Figure 4B:
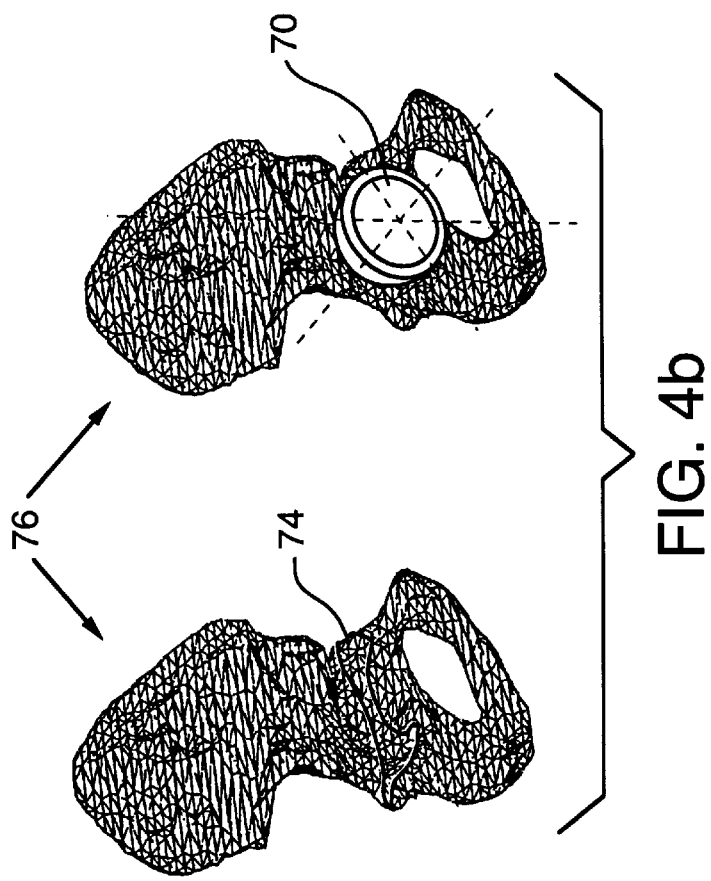
Figure 5C:
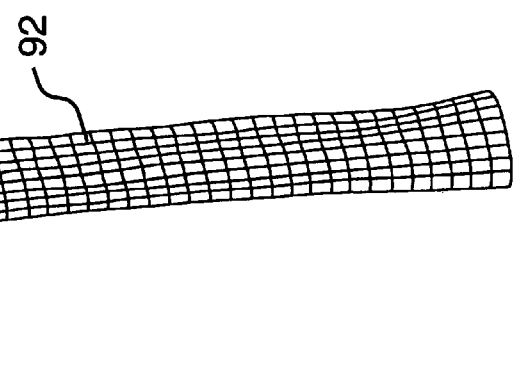
FIGS. 5(a–c) show the creation of the femur model using two dimensional scans of the femur (a), from which skeletal geometric data is extracted as shown in (b) and used to create the femur model (c)
Figure 5B:
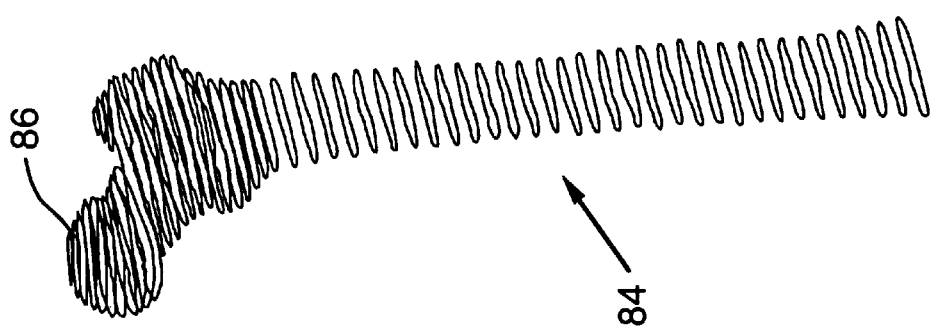

The operation of the apparatus 10 will now be discussed with reference to its use in a THR procedure. Generally, an acetabular cup 70 (FIG. 8) having a cup liner 72 in a convex portion thereof is implanted in an acetabulum 74 (FIG. 4b) of a pelvis 76. In addition, a femoral implant 78 (FIG. 7) having a head, or ball, 80 and a neck, or shaft, 82 is implanted into a femur 84. The femur 84 has a head portion 86 (FIG. 5) that is removed to facilitate the implantation. A bore 88 is drilled in the femur 84 into which the femoral implant 78 is placed. The femoral neck 82 is secured in the bore 88 in a position to allow the femoral head 80 to cooperate with the cup liner 72 in the acetabular cup 70.

Figure 4A:
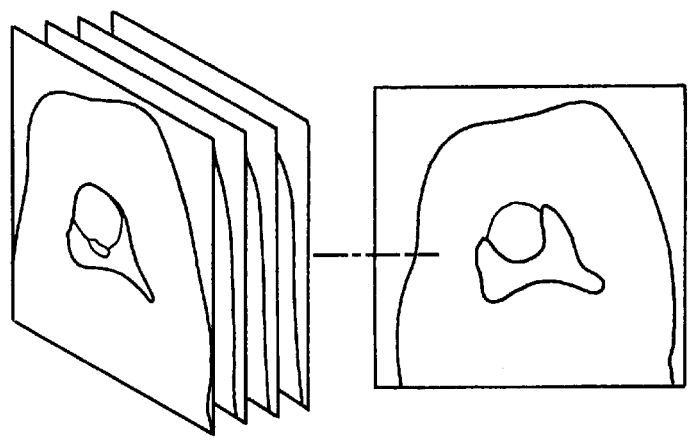
Figure 5A:
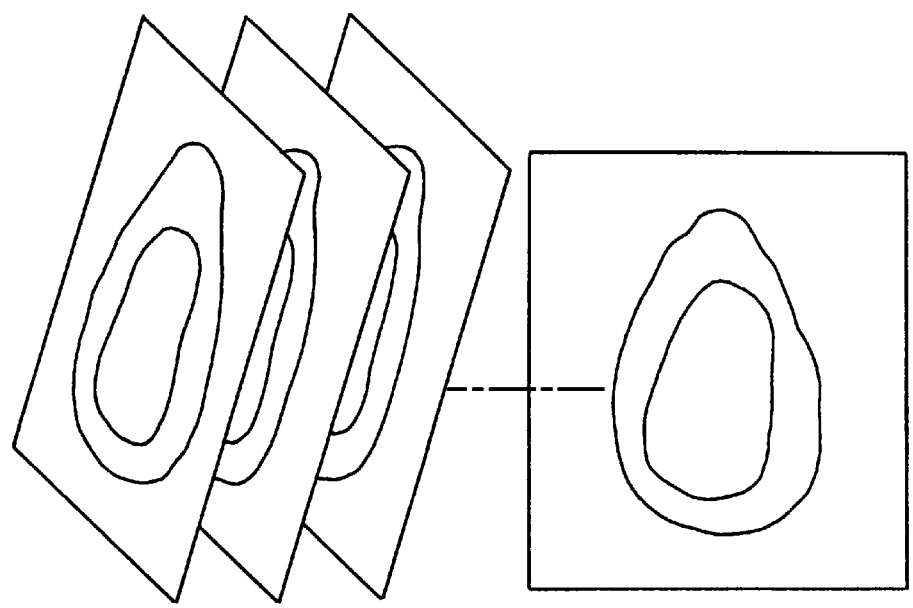

In accordance-with step 40, skeletal structure data is obtained on the femur and pelvic regions of the patient, preferably via CT scans as shown in FIG. 4(a) and 5(a), respectively, from the skeletal data source 13. The CT scans are either manually or automatically inputted in the computer system 20 (FIGS. 4(b) and 5(b)) and used to create geometric surface models 90 and 92 of the patient's pelvis 76 and femur 84 (FIGS. 4(c) and 5(c)), respectively as per step 42.

Figure 6:
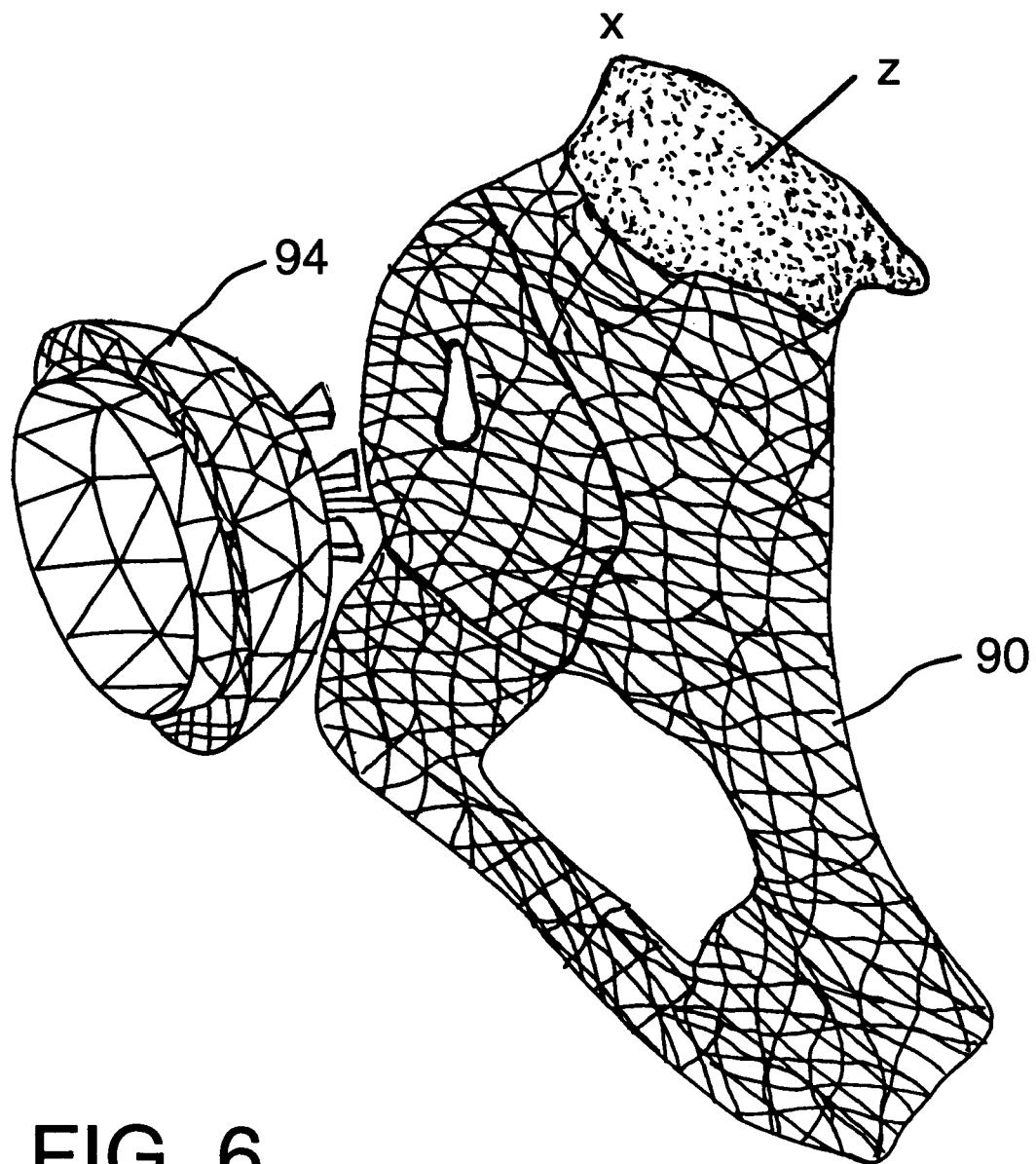
FIG. 6 shows the sizing of the acetabular cup in the pelvic model.
Figure 7:
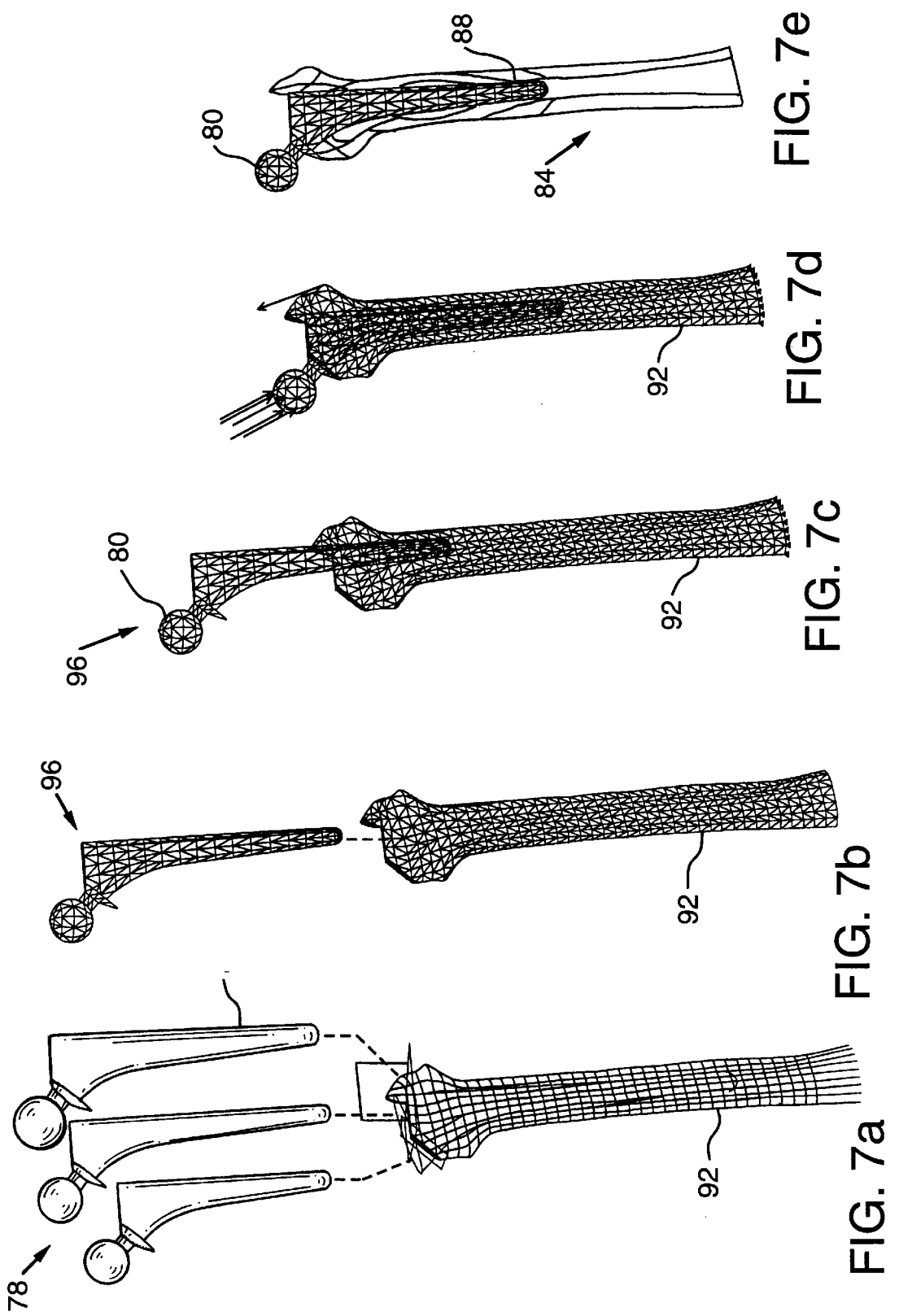
FIGS. 7(a–e) show the creation of different sized femoral implant models (a) and the fitting of the femoral implant model into a cut femur (b–e)

Geometric models 94 and 96 of the acetabular cup 70 and an femoral implant 78, shown in FIGS. 6 and 7, respectively, are created either manually or in an automated fashion using conventional computer assisted design modelling techniques with implant design or manufacturing data. The size of the acetabular cup 70 can be determined automatically based on the size of the acetabulum 74 determined from the pelvis model 90, the skeletal data or can be manually input. Similarly, the femoral implant 78 can be manually sized to cooperate with the selected acetabular cup 70 using standard implant components or the sizing of the head 80 and neck 82 of the femoral implant 78 can be customized to fit the femur 84 using the femoral implant model 96 and the femur model 92 as shown in FIGS. 7(a–e). One skilled in the art will appreciate that the computer system 20 in performing step 42 can be programmed using separate or combined software routines to create the geometric surface models of the patient's anatomy and the implant components.

The computer system 20 uses the geometric model 90 of the patient's pelvis 76, the model 92 of the patient's femur, the model 94 of the acetabular cup 70, and model 96 of the femoral implant 78 to perform simulated biomechanical testing of the acetabular cup 70 and the femoral implant 78 implanted at various test positions in the acetabulum 74 and femur 84, respectively, according to step 44. For example, in the case of femoral neck 82—cup liner 72 impingement, shown in FIG. 8, the important parameters in evaluating the prosthetic range of motion are the head 80 to neck 82 ratio of the femoral implant 78, the position, including angular orientation, of the acetabular cup 70 and the relative position of the femoral implant 78 with respect to the cup 70.

Figure 8:
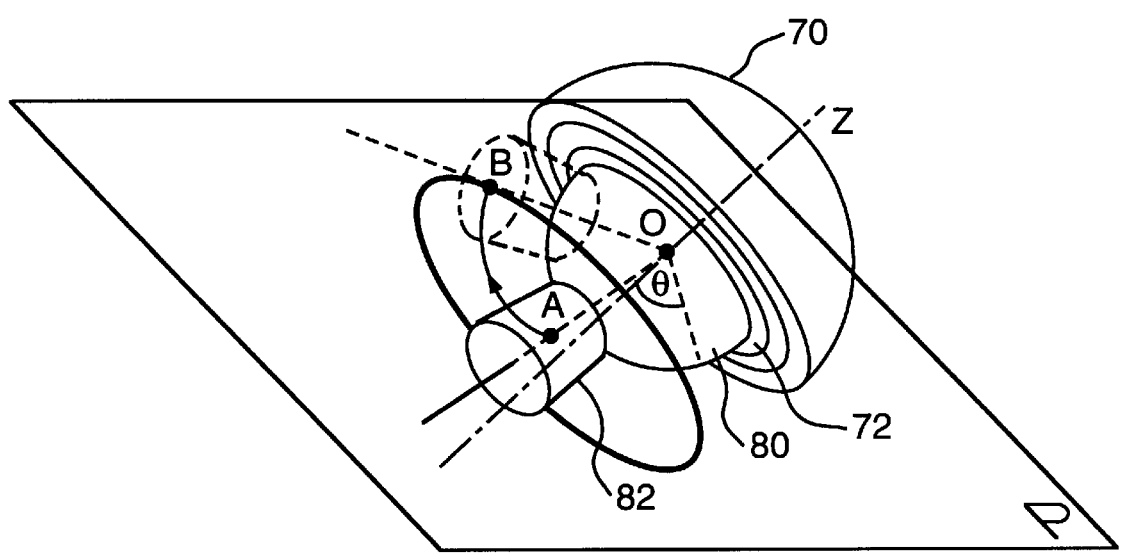
FIG. 8 is a schematic drawing showing the range of motion of a femoral shaft and the impingement (in dotted lines) of a femoral shaft on an acetabular cup.

While the present invention is applicable to non-axisymmetric acetabular implants (i.e. hooded liners, non-neutral liners) and femoral necks (i.e. non-symmetric cross sections), the following discussion of an axisymmetric acetabular cup and femoral neck alignment case is presented to ease the explanation of the concepts. If the center of rotation in the acetabular cup 70 coincides with the center of the head 80 of the femoral implant 78, as shown in FIG. 8, the angle Θ between the axis of symmetry Z of the acetabular cup 70 and the line of impingement OB defines the allowable angle of motion. The limits of impingement create a cone within which the axis of the femoral neck (line OA) can move without the femoral neck impinging upon the cup liner 72.

The position of the neck axis with respect to the cone can be evaluated by observing its intersection with a plane P placed at an arbitrary distance normal to the Z axis. The cross section of the cone defines the impingement circle (if, as stated above, both the liner 72 and the neck 82 are axisymmetric), and the path of the axis of the femoral neck 82 defines a curve in the plane P. In FIG. 8, the axis of the femoral neck 82 begins at point A and moves along the path AB to point B at which point the femoral neck 82 impinges upon the cup liner 72.

Figure 9B:
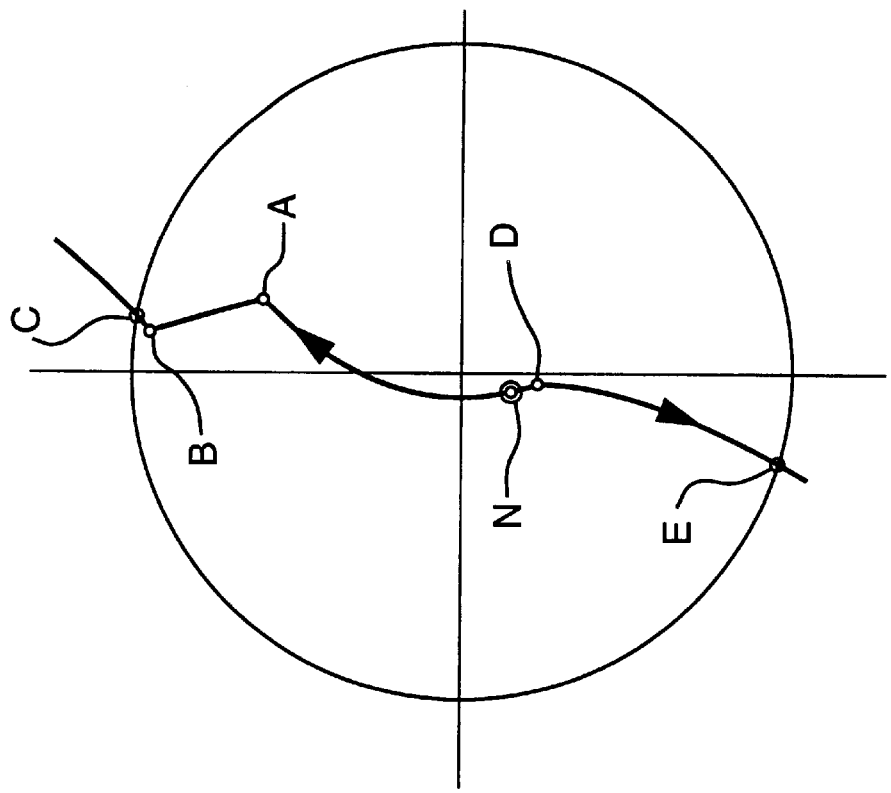
FIGS. 9(a–b) shows the range of motion results from biomechanical simulation of two respective acetabular cup orientations.
Figure 9A:
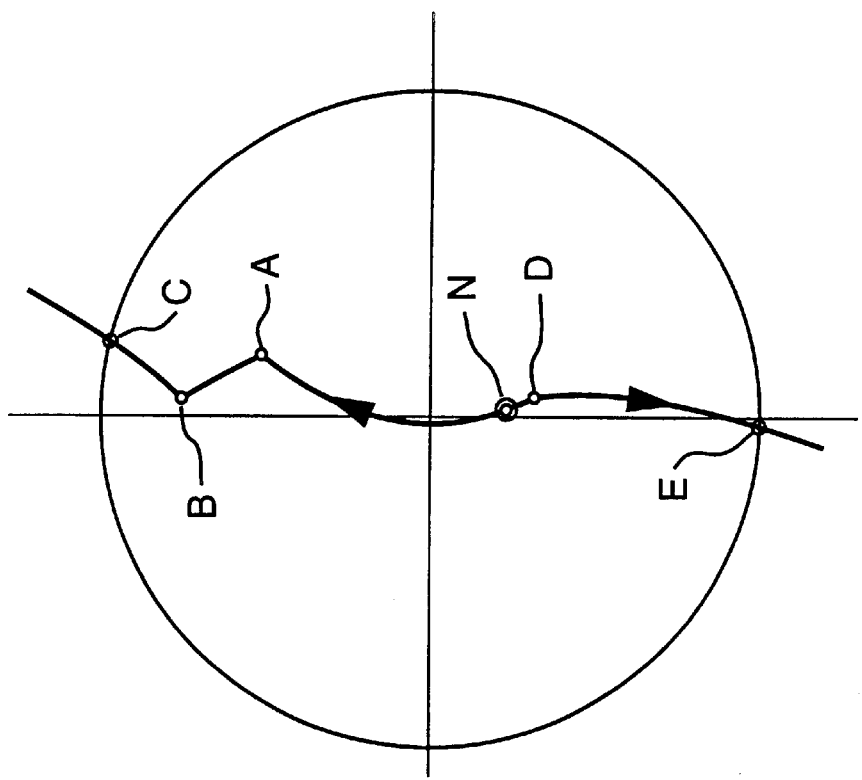

The motion of the femoral neck 82 can be derived from (and expressed as a function of) the physiological movement of the leg, described in terms of combined flexion, extension, abduction, adduction, and external and internal rotation. FIGS. 9(a) and 9(b) show an example of range of motion (ROM) simulation for two different cup orientations and for two identical sets of ROM exercises: (I) 90° flexion (A)+15° adduction (B)+ maximum internal rotation (C) and (II) 10° extension (D)+ maximum external rotation (E). As a result of reorienting the cup from 45° abduction+15° flexion (FIG. 9(a)) to 50° abduction+5° flexion (FIG. 9(b)), maximum internal rotation at the impingement point C is reduced from 15.7° to 4.3° in exercise I and maximum external rotation at the impingement point E is increased from 45.8° to 55.8° in the exercise II. In accordance with step 48, the implant position is determined by comparison of the calculated range of motion of the femoral implant 78 in the acetabular cup 70 with the predetermined range of motion. See "Simulation of Implant Impingement and Dislocation in Total Hip Replacement", Jaramaz et al., Computer Assisted Radiology, $10^{th}$ International Symposium and Exhibition, Paris, June, 1996, which is incorporated herein by reference.

In the execution of the intra-operative procedure 60, the implant position is identified in the pelvic model 90 prior to surgery as in step 52. During the surgical procedure, the pelvis 76 of the patient is exposed. One of the tracking targets 34, a pelvic target, is attached to the pelvic region, as shown in FIG. 3. Preferably, the target 34 is attached in close proximity to the acetabulum 74 to provide data as close to the area of interest as possible without becoming an impediment to the surgical procedure. The close proximate placement of the target 34 provides an additional benefit of minimizing the extent to which the pelvis must be exposed during the procedure. Positional data from discrete locations on the patient's pelvis 76 and femur 84 are taken and provided as input to the navigational guidance software 16 according to step 54.

Figure 10A:
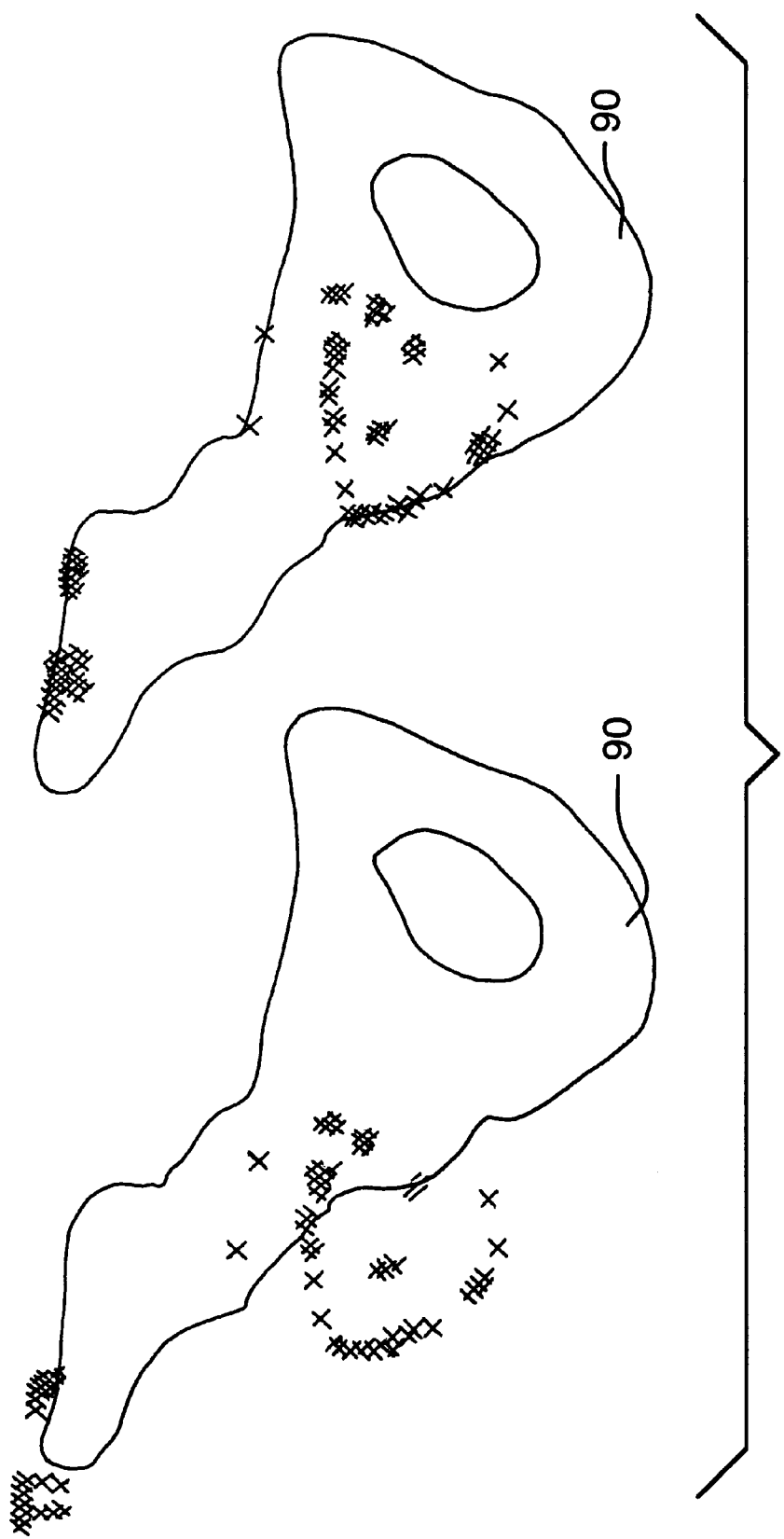
FIGS. 10 (a) and (b) show the registration of the pelvis and femur.
Figure 10B:
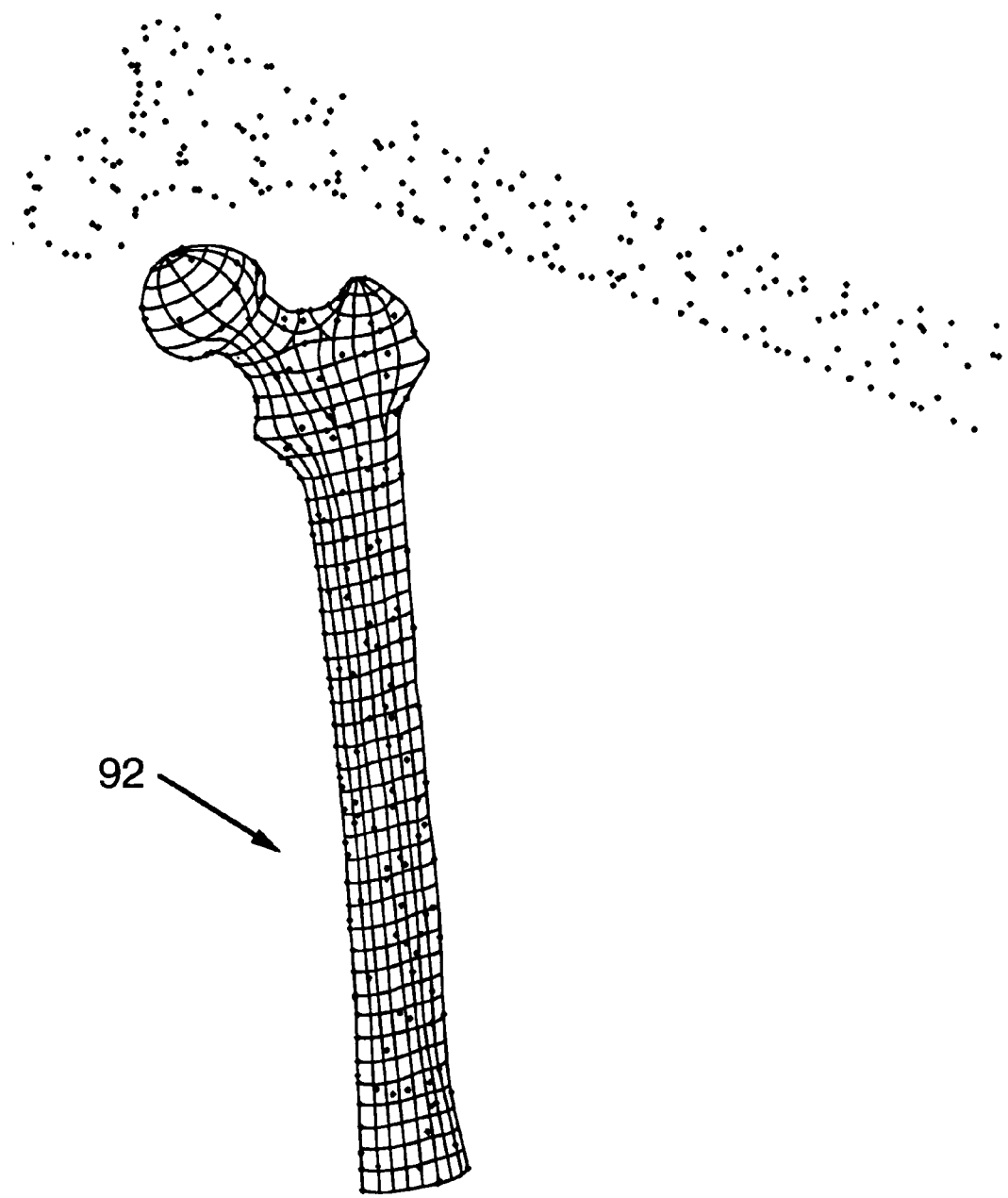

The intra-operative positional data is registered with the pelvic model 90 and femur model 92, as shown in FIGS. 10(a) and (b), to align the models with the intra-operative position of the patient's pelvis 76 and femur 84, respectively. During the acquisition of discrete registration point positional data from the pelvis 76, the tracking device 30, via camera 32, is used to track the pelvic target. The pelvic target position data is used in combination with the transformation developed using the registration data provide a spatial correspondence between pre-operative CT coordinates (i.e. pelvic model) and the intra-operative coordinates (i.e. measurements of the patient's pelvis relative to the pelvic target). Intra-operative tracking of the acetabular cup 70 is also performed relative to the pelvic target.

The position of the acetabular cup 70 prior to implantation is preferably tracked by attaching at least one other tracking target 34, a second target, to a cup insertion tool 98, as shown in FIG. 3, and mathematically relating the position of the second target 34 to the position of the cup 70. In this manner, the potential for damage to the cup 70 from directly mounting the target 34 to the cup 70 is eliminated. In addition, the target 34 can be placed on the tool 98 so as to not obscure the medical practitioner's view of the surgical area. Preferably, a third, or reference, target 34 is positioned to allow for spatial orientation of the operating room.

Guidance in the placement of the acetabular cup 70 is provided by the navigational software 16 in the computer 20 which displays on the monitor 22 near real time position tracking of the cup 70 relative to the to the pre-operatively specified implant position. Once the cup 70 is aligned with the implant position, the cup 70 is in the pre-operatively planned orientation.

A series of tests were developed and performed to assess the ability of the apparatus 10 to correctly predict the impingement of the femoral neck 82 with acetabular cup liner 72. The series of tests were developed because the testing described in available references did not include experimental parameters, such as neck size and the orientation of the fomeral neck axis, necessary to evaluate the biomechanical simulator. The testing was performed using a laboratory prototype of the apparatus 10, known as the HipNav™ system. Details of the testing are presented in Jaramaz et al., "Range of Motion After Total Hip Arthroplasty: Experimental Verification of the Analytical Simulator", Carnegie Mellon University, Robotics Institute Technical Report CMU-RI-TR-97-09 (Feb. 1997) and Jaramaz et al., "Simulation of Implant Impingement and Dislocation in Total Hip Replacement", Computer Assisted Radiology, $10^{th}$ International Symposium and Exhibition, Paris, June, 1996, both of which are incorporated herein by reference.

Although the present invention has been described with specific examples directed to hip replacement and revision, those skilled in the art will appreciate that the method and apparatus may be employed to implant a component in any joint. The skilled artisan will further appreciate that any number of modifications and variations can be made to specific aspects of the method and apparatus of the present invention without departing from the scope of the present invention. Such modifications and variations are intended to be covered by the foregoing specification and the following claims.

What is claimed is:

1. An apparatus for facilitating the implantation of an artificial component in a joint, comprising:
   a pre-operative geometric planner; and
   a pre-operative kinematic biomechanical simulator in communication with said pre-operative geometric planner wherein said pre-operative kinematic biomechanical simulator outputs a position for implantation of the artificial component.

2. The apparatus of claim 1, further comprising an intra-operative navigational module in communication with said pre-operative kinematic biomechanical simulator.

3. The apparatus of claim 2, further comprising a tracking device in communication with said intra-operative navigational module.

4. The apparatus of claim 1, wherein said pre-operative geometric planner is responsive to a skeletal data source.

5. The apparatus of claim 4, wherein said skeletal data source includes geometric data.

6. The apparatus of claim 4, wherein said pre-operative geometric planner outputs at least one geometric model of the component and the joint.

7. The apparatus of claim 6, wherein said pre-operative kinematic biomechanical simulator is responsive to said geometric model.

8. The apparatus of claim 7, wherein said implant position includes an angular orientation of the component.

9. The apparatus of claim 3, wherein said tracking device is selected from the group consisting of an acoustic tracking system, shape based recognition tracking system, video-based tracking system, mechanical tracking system, electro-magnetic tracking system and radio frequency tracking system.

10. A system, comprising:
    a computer system including;
       a pre-operative geometric planner; and
       a pre-operative kinematic biomechanical simulator in communication with said pre-operative geometric planner wherein said pre-operative kinematic biomechanical simulator outputs a position for implantation of an artificial component in a joint; and a tracking device in communication with said computer system.

11. The system of claim 10, further comprising at least one display monitor in communication with said computer system.

12. The system of claim 10, further comprising at least one controller in communication with said computer system.

13. The system of claim 10, wherein said tracking device includes at least one camera.

14. The system of claim 10, wherein said tracking device includes at least one target.

15. The system of claim 10, wherein said computer system further includes an intra-operative navigational module in communication with said pre-operative kinematic biomechanical simulator.

16. A computer-assisted method comprising determining an implant position of an artificial component in a joint by utilizing a predetermined range of motion and a calculated range of motion determined from a simulated movement of said joint and component models from a test position.

17. A method for determining an implant position for at least one artificial component in a joint, comprising:

creating at least one model of the joint and at least one model of the artificial component;

calculating a range of motion based on a simulated movement of the joint with the artificial component in a test position; and determining the implant position based on said calculated range of motion and a predetermined range of motion.

18. The method of claim 17 further comprising simulating movement of the joint with the artificial component in a test position using said models.

19. A method for facilitating an implant position for at least one artificial component in a joint, comprising:

creating at least one model of the joint and at least one model of the artificial component;

calculating a range of motion based on a simulated movement of the joint with the artificial component in a test position;

determining the implant position based on said calculated range of motion and a predetermined range of motion;

aligning said model of the joint with the joint and said model of the artificial component with the artificial component; and tracking the artificial component and the joint.

20. The method of claim 19 further comprising simulating movement of the joint with the artificial component in a test position using said models.

21. The method of claim 19 wherein aligning said model of the joint with the joint and said model of the artificial component with the artificial component includes aligning said model of the joint with the joint and said model of the artificial component with the artificial component based on positional tracking data representative of the position of the joint and the artificial component.

22. The method of claim 19 wherein tracking the artificial component and the joint includes tracking the artificial component and the joint to maintain alignment of the joint model with the joint and to determine the artificial component position relative to the implant position in the joint.

23. A computer-readable medium having stored thereon instructions which, when executed by a processor, cause the processor to perform the step of determining an implant position of an artificial component in a joint by utilizing a predetermined range of motion and a calculated range of motion determined from a simulated movement of said joint and component models from a test position.

24. A computer-readable medium having stored thereon instructions which, when executed by a processor, cause the processor to perform the steps of:

creating at least one model of a joint and at least one model of an artificial component;

calculating a range of motion based on a simulated movement of the joint with the artificial component in a test position; and determining the implant position based on said calculated range of motion and a predetermined range of motion.

* * * * *